(12) United States Patent
Tulkis

(10) Patent No.: US 8,034,059 B2
(45) Date of Patent: Oct. 11, 2011

(54) ACETABULAR SHELL REMOVAL INSTRUMENT

(75) Inventor: Peter Tulkis, Paramus, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 12/781,972

(22) Filed: May 18, 2010

(65) Prior Publication Data

US 2010/0228259 A1 Sep. 9, 2010

Related U.S. Application Data

(62) Division of application No. 11/068,671, filed on Mar. 1, 2005, now Pat. No. 7,763,031.

(51) Int. Cl.
*A61B 17/88* (2006.01)
(52) U.S. Cl. .............................. 606/99; 606/91
(58) Field of Classification Search .............. 606/80–82, 606/85, 91, 99, 100
See application file for complete search history.

(56) References Cited

U.S. PATENT DOCUMENTS

| | | | |
|---|---|---|---|
| 2,070,281 A | 2/1937 | Leggiardo | |
| 3,461,875 A | 8/1969 | Hall | |
| 3,628,522 A | 12/1971 | Kato | |
| 3,943,916 A | 3/1976 | Vadas | |
| 4,802,468 A * | 2/1989 | Powlan | 606/81 |
| 4,903,692 A * | 2/1990 | Reese | 606/99 |
| 5,112,338 A | 5/1992 | Anspach, III | |
| 5,290,315 A | 3/1994 | DeCarlo, Jr. | |
| 5,830,215 A * | 11/1998 | Incavo et al. | 606/79 |
| 5,913,858 A | 6/1999 | Calandruccio et al. | |
| 5,938,701 A | 8/1999 | Hiernard et al. | |
| 6,013,082 A | 1/2000 | Hiernard et al. | |
| 6,022,357 A | 2/2000 | Reu et al. | |
| 6,063,124 A | 5/2000 | Amstutz | |
| 6,152,930 A | 11/2000 | Mastrorio | |
| 6,187,012 B1 | 2/2001 | Masini | |
| 6,565,575 B2 | 5/2003 | Lewis | |
| 7,008,430 B2 | 3/2006 | Dong et al. | |
| 2003/0100905 A1 | 5/2003 | Mears | |
| 2003/0212402 A1 | 11/2003 | White et al. | |

* cited by examiner

*Primary Examiner* — Eduardo C. Robert
*Assistant Examiner* — Julianna N. Harvey
(74) *Attorney, Agent, or Firm* — Lerner, David, Littenberg, Krumholz & Mentlik, LLP

(57) ABSTRACT

An acetabular shell or cup removal instrument is disclosed. The instrument includes a first end capable of being received within an acetabular cup and a cutting element pivotally attached. Cutting motion is provided to the instrument by a powered handpiece, so that the cutting element is capable of cutting a bone surface adjacent to an outer surface of the acetabular cup when the first end is within the acetabular cup.

17 Claims, 20 Drawing Sheets

ACETABULAR SHELL REMOVAL INSTRUMENT

CROSS-REFERENCE TO RELATED APPLICATIONS

This application is a divisional of U.S. application Ser. No. 11/068,671, filed on Mar. 1, 2005, the disclosure of which is incorporated herein by reference.

BACKGROUND OF THE INVENTION

One area of the body which is highly prone to chronic pain and degeneration of normal function is the hip joint. Whether caused by disease, aging, overuse, or injury, a significant portion of the population suffers from ailments relating to the hip. An often utilized last resort solution to problems pertaining to the hip joint is total hip replacement ("THR") surgery. Generally, THR surgery consists of the replacement of the existing ball and socket of the hip joint with prosthetic replacements. The head of the femur (i.e.—the ball) is typically removed and replaced with a femoral component made of biocompatible material, which mirrors the structure of the original bone. The acetabulum (i.e.—the socket) is typically reamed and fitted with a prosthetic acetabular cup component that corresponds and cooperates with the femoral component. This prosthetic acetabular cup component often times includes an outer shell constructed of a metallic material and an insert constructed of plastic, ceramic or metal received within the outer shell. In many cases, the acetabular cup component is anchored in the bone through the use of cements and/or bone growth technology that allows for bone to grow in and around the cup. Such surgery is widely utilized and often highly successful in relieving many problems associated with the hip joint.

Regardless of the high success rate of THR surgeries, even initially successful hip replacements may require revision over time. Most often, where, injury, disease, infection, or the like may bring upon the failure. In revision surgeries, it is necessary to remove the acetabular component previously implanted in the acetabulum. As mentioned above, these components may have been cemented in place or otherwise held by bone or fibrous tissue that may have grown in and around the component. Thus, their removal requires the cutting or chipping away of cement or bone material.

Prior art devices have been proposed that attempt to lessen the difficultly associated with the removal of an acetabular component. Typically, these devices include a cutting portion and a manipulation portion that requires manual operation by the surgeon. The manipulation portion and the cutting portion are generally configured with respect to each other so as to guide the cutting portion in and around the outer surface of the acetabular cup. While these prior art devices provide a guide for cutting that may indeed aid in the removal of the acetabular cup portion, they require manual operation and significant time to complete the removal step. For example, prior art curved osteotomes, and U.S. Pat. Nos. 5,803,215 and 6,565,575 relate to manual acetabular cup removal instruments. However, it is advantageous to reduce removal time by using a power driven tool.

Therefore, there exists a need for an apparatus capable of removing an acetabular cup from the acetabulum during a revision THR surgery in a fast, easy and reliable fashion without requiring significant exertion on the part of a surgeon.

SUMMARY OF THE INVENTION

A first aspect of the present invention is a powered apparatus for removing an acetabular cup from an acetabulum of a patient. The apparatus according to an embodiment of this first aspect includes an elongate shaft having a first end and a second end, the first end capable of being received within an acetabular cup. A cutting element may be attached to the elongate shaft adjacent the first end for movement towards the acetabulum, the cutting element being capable of cutting a bone or cement surface adjacent to an outer surface of the acetabular cup when the first end is within the acetabular cup. And, a powered handpiece may be connected to the second end of the elongate shaft, the powered handpiece capable of providing a cutting motion to the cutting element. Other embodiments may include a cutting element pivotally attached to the elongate shaft for pivotal movement towards the acetabulum. In certain embodiments, the cutting motion may be an oscillating motion, including an oscillating motion that is approximately four degrees in a clockwise direction and four degrees in a counter-clockwise direction. In other embodiments, the apparatus may include an engagement element attached to the first end of the elongate shaft for engaging the acetabular cup, the attachment may be a removable attachment. Still further embodiments may include a handle slidably engaged with the elongate shaft capable of pivoting the cutting element.

Another embodiment of the present invention is an instrument for removing an implanted acetabular cup having a part-spherical outer surface from an acetabulum. The instrument according to this embodiment may include an elongate shaft having a first end for engaging the implanted acetabular cup and an actuator mounted on the shaft for at least partial rotation therearound. A cutting element may be pivotally coupled to the shaft adjacent the first end at a point radially offset from the shaft, the cutting element pivotable towards the acetabulum along an arcuate path conforming to the part-spherical outer surface of the acetabular cup. A connector may be coupled to the actuator and the cutting element for pivoting the cutting element towards the acetabulum upon movement of the actuator, the movement of the actuator independent of the partial rotation of the actuator in the shaft. In accordance with other embodiments, the actuator may have an inner bore for receiving the shaft and a recess open to the bore engaging a radially outwardly extending finger on the shaft. The recess may have a dimension greater than the finger to allow the at least partial rotation of the actuator or the shaft.

Another embodiment of the present invention is another apparatus for removing an acetabular cup from an acetabulum. The apparatus according to this embodiment includes an instrument capable of oscillating, the instrument having a first end and a cutting element mounted adjacent the first end. The oscillating motion of the instrument allows the cutting element to cut a bone portion around the acetabular cup when the first end is placed in the acetabular cup.

Another aspect of the present invention is a method of removing an acetabular cup from an acetabulum. The method according to this aspect includes providing a powered apparatus including an elongate shaft having a first end and a second end, a blade attached adjacent the first end, and a powered handpiece connected to the second end, placing a portion of the first end of the elongate shaft within the acetabular cup, operating the powered handpiece so as to make at least one cut in a bone surface adjacent an outer surface of the acetabular cup and removing the acetabular cup from the acetabulum. In certain embodiments, the method may further include the step of manipulating a handle engaged with the elongate shaft to determine the depth of the cut in the bone surface adjacent the outer surface of the acetabular cup. The method may also include the step of selecting an appropriately sized cutting element corresponding to the size of the acetabular cup.

Yet another aspect of the present invention is a kit for use in removing an implanted acetabular cup. The kit in accordance with this aspect includes an instrument including an elongate shaft having a first end and a second end, a powered handpiece for attachment to the second end of the elongate shaft, a plurality of engagement elements for attachment to the first end of the elongate shaft and adapted to be received within an acetabular cup, and a plurality of cutting elements for attachment adjacent the first end of the elongate shaft. Preferably, the kit includes at least one differently dimensioned engagement element and at least one differently dimensioned cutting element. It is contemplated that specific combinations of engagement elements and cutting elements may be provided and utilized to removed specific acetabular cups.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

In describing the preferred embodiments of the subject matter illustrated and to be described with respect to the drawings, specific terminology will be used for the sake of clarity. However, the invention is not intended to be limited to any specific terms used herein, and it is to be understood that each specific term includes all technical equivalents which operate in a similar manner to accomplish a similar purpose.

Figure 1:
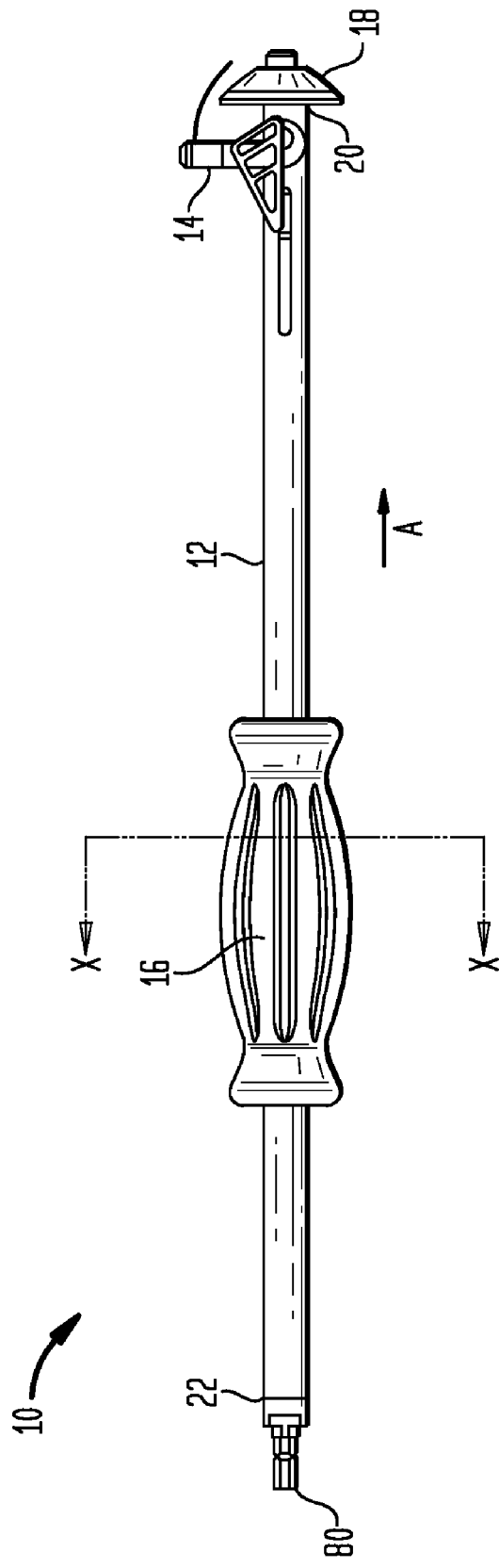
FIG. 1 is a plan view of a removal instrument according to an embodiment of the present invention.

Referring to the drawings, wherein like reference numerals represent like elements, there is shown in the Figures, in accordance with embodiments of the present invention, an acetabular shell removal instrument designated generally by reference numeral 10. In a preferred embodiment, as shown in Figures, removal instrument 10 is designed to be used in removing a previously implanted acetabular cup. Typically, this removal is done during a subsequent or revision THR surgery, performed as a result of the failure of a previous THR surgery. As best shown in FIG. 1, removal instrument 10 includes a hollow elongate shaft 12, a blade assembly 14, a handle 16, and an engagement element 18. The particular embodiment shown in the Figures is capable of aiding in the fast and easy removal of a previously implanted acetabular cup component.

Elongate shaft 12 is a substantially cylindrically shaped tubular member. Elongate shaft 12 has a second end 22 adjacent handle 16 and a first end 20 for insertion into the acetabular cup shell after a bearing or insert has been removed. As best shown in the exploded view of FIG. 2, hollow shaft 12 further includes a first elongate aperture 24, located at or near the center of shaft 12, a second elongate aperture 26 and pivot apertures 28 and 29, located at or near second end 20. Instrument 10 includes a tubular insert 30 adapted to fit within bore 31 (best shown in FIG. 6b) of hollow shaft 12. Insert 30 is shaped to fit within the hollow opening of shaft 12 (i.e.—is preferably cylindrically shaped) and includes a channel 32 extending longitudinally along its length. While the shapes of shaft 12 and insert 30 are shown as being cylindrical in nature, it is contemplated that these components can be configured and dimensioned in various fashions, with the only limitation being that they properly interact with each other and the other components of instrument 10. For example, shaft 12 may be a hollow structure having a square internal cross section, while insert 30 may be a complimentary square shape.

Figure 2:
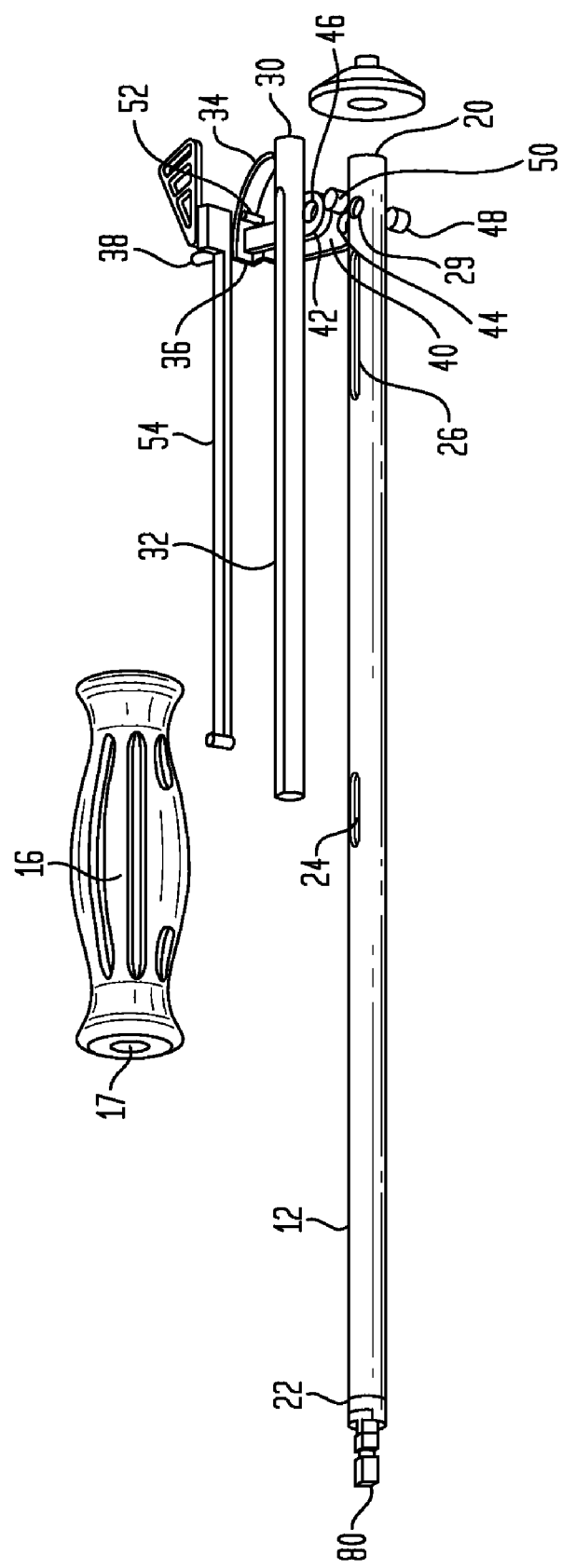
FIG. 2 is an exploded perspective view of the removal instrument shown in FIG. 1.
Figure 3:
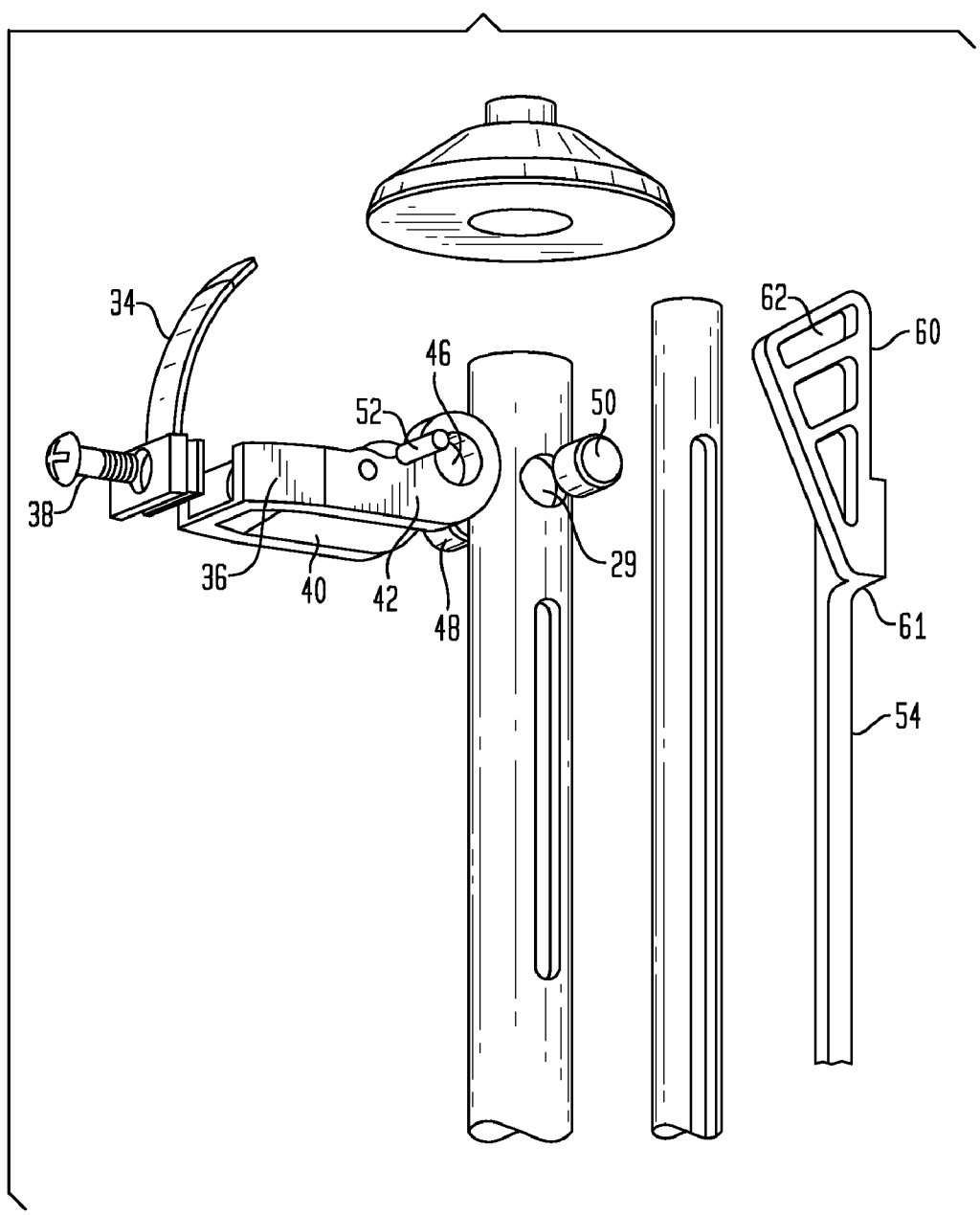
FIG. 3 is an enlarged exploded perspective view of a first end of the removal instrument shown in FIG. 2.
Figure 4:
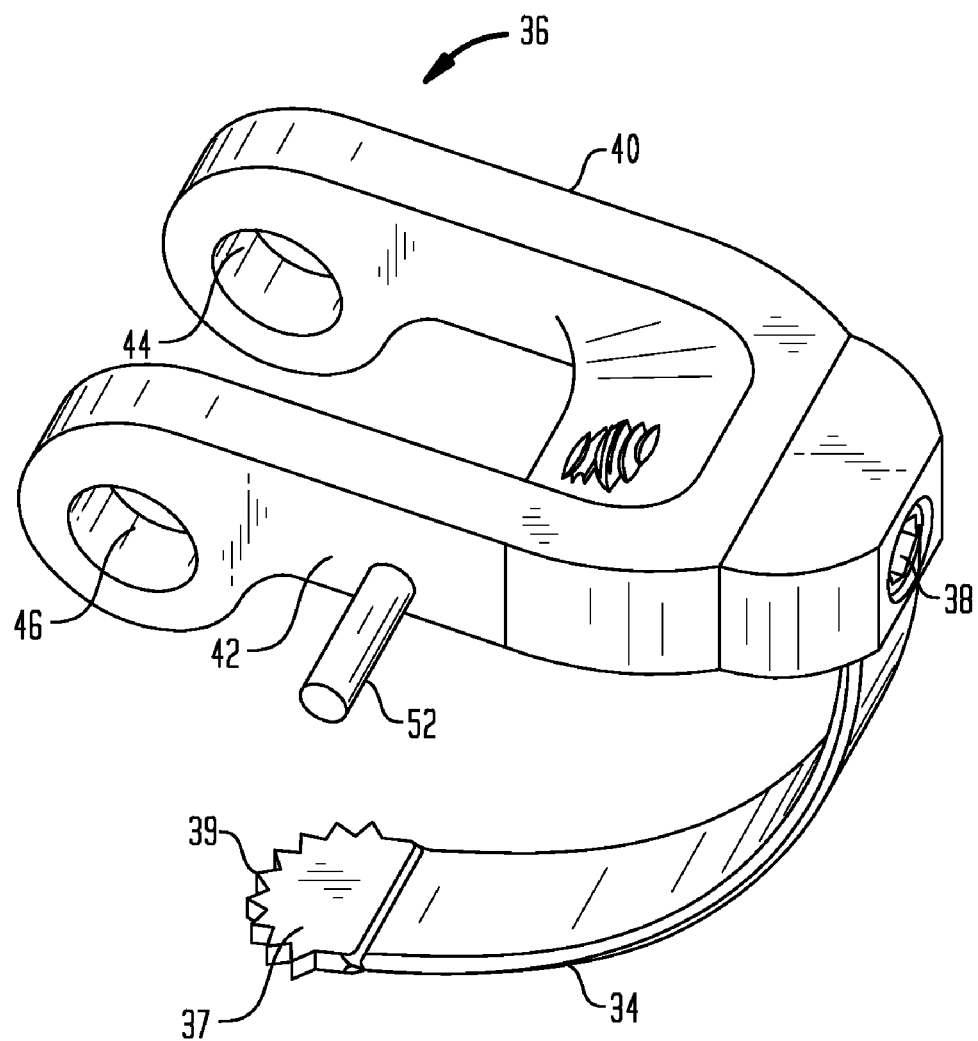
FIG. 4 is a perspective view of a portion of the blade actuation assembly of the removal instrument shown in FIGS. 1-3.
Figure 20:
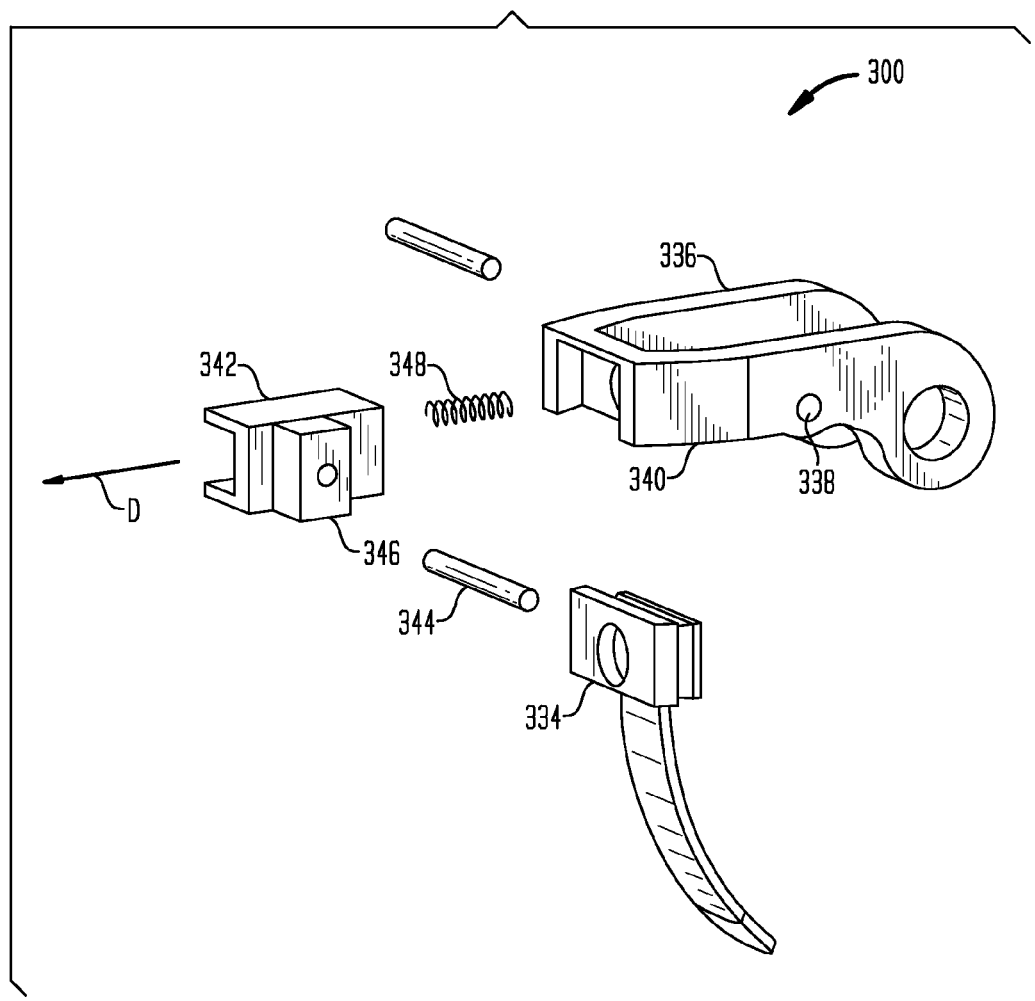
FIG. 20 is an exploded view of a quick connect device in accordance with the present invention.
Figure 21:
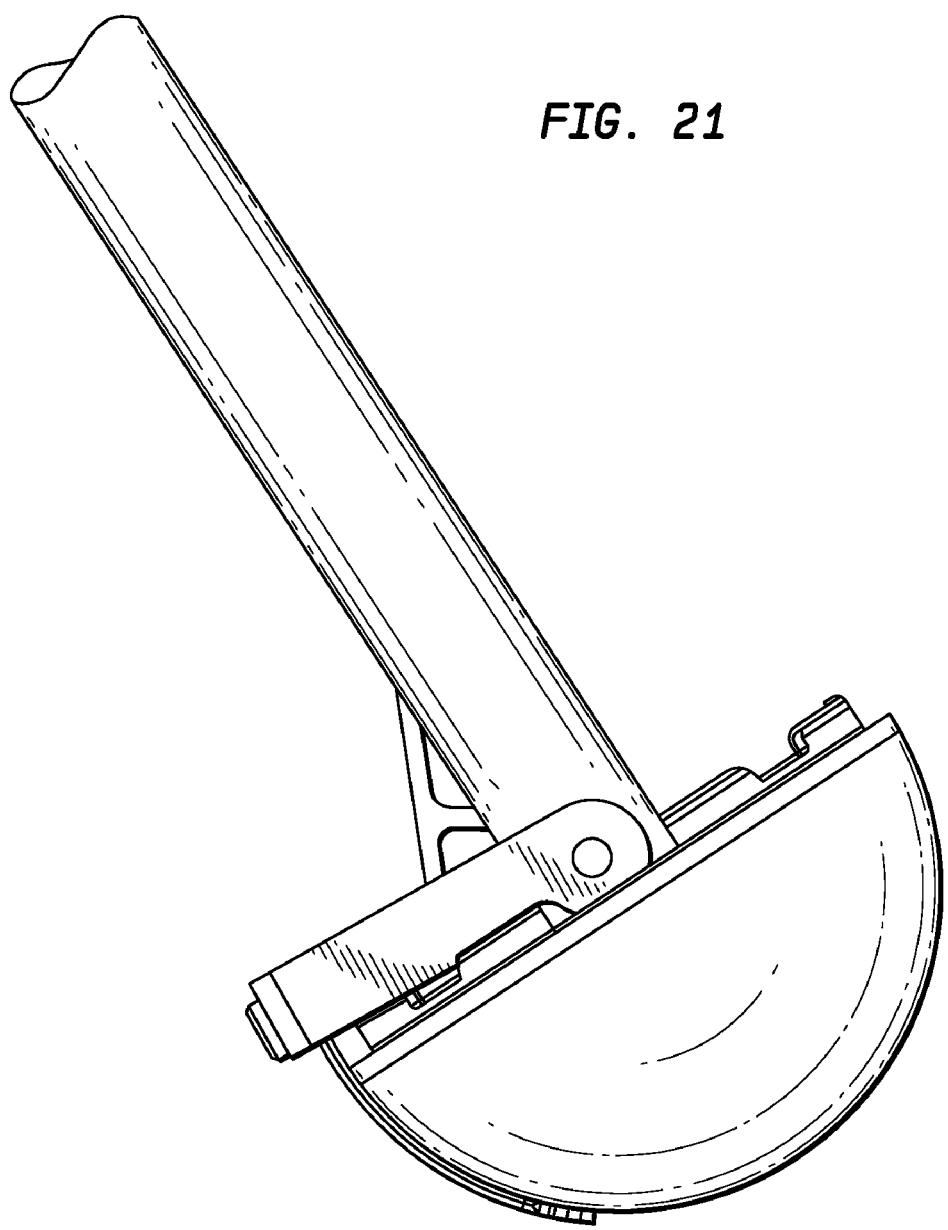
FIG. 21 is a perspective view of an embodiment of the present invention showing a blade attached through the use of a quick connect device.

As best shown in FIGS. 2 and 3, end 20 of shaft 12 includes two pivot pins 48 and 50 fixedly mounted in apertures 28 and 29 respectively. Alternatively, in other embodiments, one longer pin could be employed that extends through both apertures 28 and 29. Such a design may aid in keeping insert 30 in place, when inserted in shaft 12. In a preferred embodiment, the blade actuation assembly 14 is rotably mounted on pins 48 and 50 via a pivot element 36 (see FIG. 4). Blade actuation assembly 14 includes a cutting element in the form of a curved blade or arm removably attached to pivoting element 36 by a screw 38 or other suitable means. For example, blade 34 may be removably attached to pivoting element 36 through a mechanical cooperation such as a male/female connection, a quick connect device (as shown in FIGS. 20 and 21) or a spring detent. Blade 34 includes a cutter head 37 including a plurality of teeth 39 and is curved to match the outer curve of a shell. Pivoting element 36, shown in greater detail in FIG. 4, has spaced legs 40 and 42, each leg having an aperture 44 and 46 respectively for pivotably engaging pins 48, 50 of shaft 12. The legs are spaced so as to be capable of straddling shaft 12, with aperture 44 engaging a protrusion 48 mounted in pivot aperture 28 and aperture 46 engaging a protrusion 50 mounted in pivot aperture 29. It is noted that protrusions 48 and 50 may be fitted and retained respectively into apertures 28 and 29 by any means, including but not limited to press fitting, thread means, welding, adhesives or the like. Pivoting element 36 further includes an extension pin 52 extending from leg 42. This pin may be attached to the pivoting element in a similar manner to that of protrusions 48 and 50.

Figure 5:
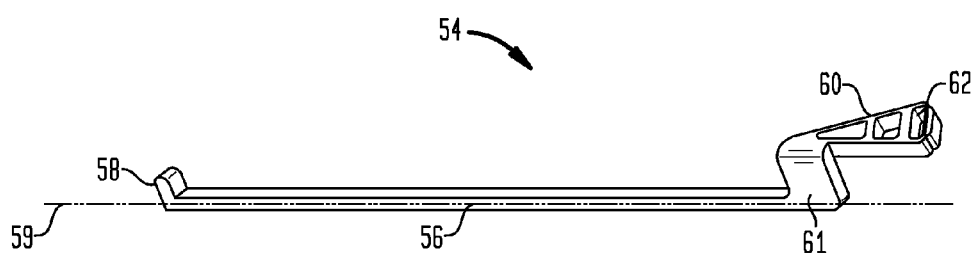
FIG. 5 is a perspective view of a slide bar of the removal instrument shown in FIG. 2.

The preferred blade actuation assembly 14 further includes slide bar 54 which cooperates with both shaft 12 and insert 30. As best shown in FIG. 5, slide bar 54 includes an axially extending elongate body 56 in the form of a bar having a finger 58 disposed on a first end and extending in a direction perpendicular to the axis 59 of bar 56, and a slotted receiver plate 60 offset on the opposite end. Receiver 60 is mounted on a flange 61, which like finger 58, extends in a direction perpendicular to axis 59 of bar 56. Receiver 60 is a generally triangularly shaped plate lying in a plane which extends parallel to axis 59. Thus, the plane of slotted plate 60 is offset from a plane containing axis 59 in the same direction as finger 58 and flange 61. Plate 60 further includes at least one elongate slot, channel or aperture 62 for engaging extension pin 52 located on pivoting element 36.

Figure 6A:
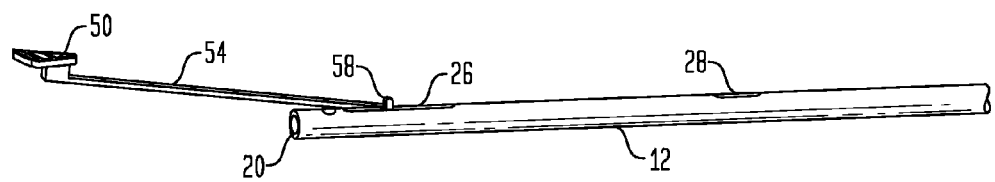
FIGS. 6a-6f depict a portion of the assembly of the slide bar of FIG. 5 into a shaft of the removal instrument shown in FIG. 1.
Figure 6B:
Figure 6C:
Figure 6D:
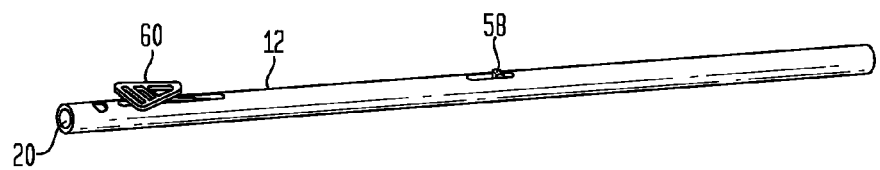
Figure 6E:
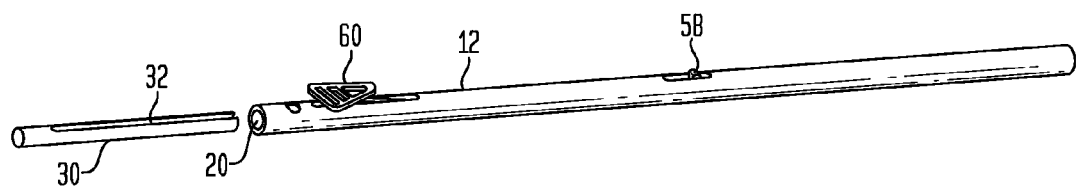
Figure 6F:

Slide bar 54 is configured and dimensioned to be received within bore 31 and between the inner walls of shaft 12 and insert 30. FIGS. 6a through 6f depict the assembly and cooperation between slide bar 54, elongate shaft 12 and insert 30. During assembly, slide bar 54 is inserted into elongate aperture 26 and slid into interior bore 31 of shaft 12 until finger 58 extends through aperture 28 with receiver plate 60 remaining outside of shaft 12 adjacent aperture 26. While FIGS. 6a through 6c illustrate various other positions of slide bar 54 with respect to shaft 12, during the assembly procedure, FIG. 6d depicts this latter position. Preferably, the various components of instrument 10 are designed such that cooperation between shaft 12 and bar 54 allows the movement of finger 58 within bore 31. Essentially, proper clearance is provided to allow for the assembled position shown in FIG. 6d to be achieved. FIGS. 6e and 6f show the further step of insertion of insert 30 into open first end 20 of shaft 12. Insert 30 is positioned during the assembly so that channel 32 aligns with and receives the elongate body portion 56 of slide bar 54. Thus, insert 30 acts as a guide for bar 54 and prevents it from buckling when a compressive force is applied. Furthermore, channel 32 of insert 30 is sized in order to situate slide bar 54 at the proper depth with respect to shaft 12. Once assembled, slide bar 54 remains capable of sliding with respect to both shaft 12 and insert 30. Thus, in the fully assembled condition, slide bar 54 is capable of sliding in a longitudinal direction along elongate shaft 12, with its motion being limited only by the length of either aperture 26 or 28, whichever is shorter. In the preferred embodiment, slot 28 is shorter and the engagement of finger 58 and the ends of slot 28 act to limit the movement of bar 54 in the axial direction.

Figure 7:
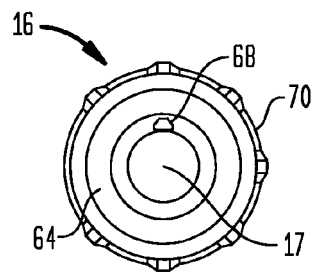
FIG. 7 is a cross sectional view taken along lines x-x of a handle of the removal instrument shown in FIG. 1.

Continuing with the assembly of instrument 10, pivoting element 36 is pivotally attached to pins 48, 50 shaft 12, as discussed above, so that in full assembly, extension pin 52 resides in aperture 62 of receiver plate 60. This configuration allows for the rotation of pivoting element 36 about an axis extending through apertures 28 and 29 and pivot pins 48, 50, as a direct result of the sliding motion of slide bar 54 within bore 31. As shown in the cross sectional depiction of FIG. 7, handle 16 includes a body 64 having a bore 17 with a diameter sized to slidably receive shaft 12, and a recess 68 open to bore 17 for tightly engaging finger 58 of slide bar 54 in the axial direction and allowing for movement of finger 58 within slot 28 on movement of handle 16 along shaft 12. Slot 68 is preferably wider in a direction perpendicular to axis 59 at one end (not shown) to allow for the oscillating motion of the entire assembly including shaft 12 within handle 16. An outer surface 70 of handle 16 may be ergonomically designed to better suit grasping by a surgeon. Referring again to FIG. 1, sliding movement of handle 16 in the direction of arrow A, causes slide bar 54 to move in an axial direction, which in turn, rotates pivoting element 36 in a clockwise direction in FIG. 1. This rotation causes blade 34 to extend deeper into a bone surface. It should be recognized that operation of handle 16 in the opposite direction than that depicted by arrow A will cause pivoting element 36 to rotate in a counter clockwise direction in FIG. 1, This system will be discussed further below.

Figure 8:
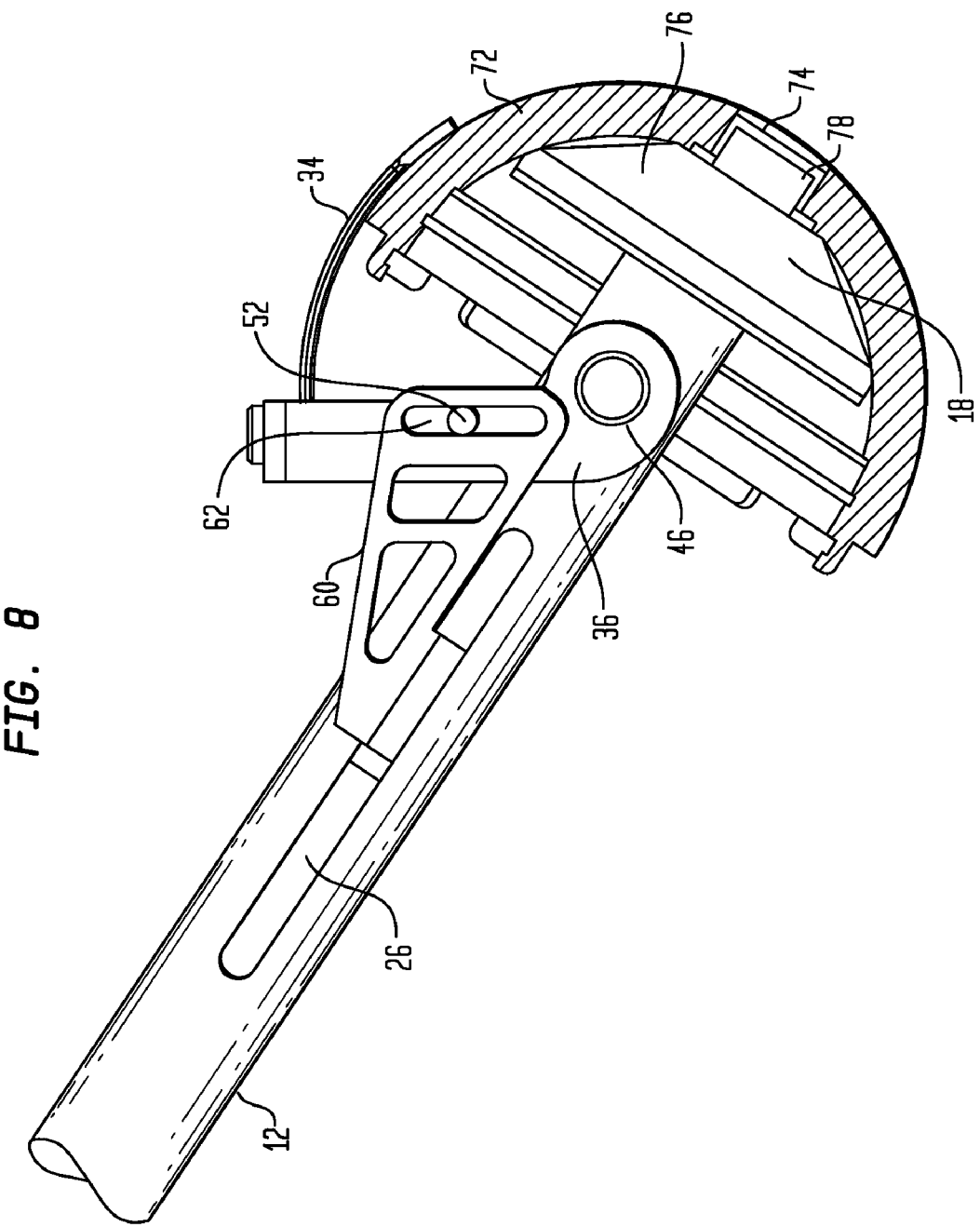
FIG. 8 is a view depicting the cooperation between the removal instrument shown in FIG. 1 and an acetabular cup, with a portion of the acetabular cup cut away.

Engagement element 18, as best shown in the cut away view of FIG. 8, is designed to engage an acetabular cup outer shell 72 having a centering hole 74. Engagement element 18, as shown in the drawings, includes a conical body 76 and a cylindrical portion 78. In operation, engagement element 18 is placed into a previously implanted acetabular cup 72. Typically, cups of this type include a centering hole 74. Cylindrical portion 78 is sized and shaped to be capable of being rotatably received within hole 74. The length portion 78 is such that it allows conical body 76 to come into engagement with the interior of cup 72 (i.e. cylinder 78 does not extend beyond the outer surface of shell 72). The cooperation between engagement element 18 and cup 72 causes axis 59 of instrument 10 to align with the polar axis of shell 72 such that blade 34 may be moved into and out of engagement with a bone surface surrounding the outer hemispherical surface of cup 72. Essentially, as best shown in FIG. 8, engagement element 18 seats instrument 10 in acetabular cup 72 and the remainder of the components are configured and dimensioned so that blade 34, is operable to cut closely around the exterior of cup 72.

It is noted that the specific shape and dimensions of the embodiment of engagement element 18 shown in the drawings prevents the pivoting of instrument 10. Thus, once seated in acetabular cup 72, instrument 10 is axially aligned and remains aligned throughout operation. However, engagement element 18 may be various shapes in different embodiments. For example, in certain embodiments, engagement element 18 may be designed so as to be capable of positively engaging with and/or locking into acetabular cup 72. In these embodiments, engagement element 18 may engage acetabular cup 72 by any means, including cooperating threaded elements, expanding collets, or other locking features like those present on well known acetabular inserts. It is contemplated that engagement element 18 may also be attached in any suitable fashion to first end 20 of elongate shaft 12, including being removably attached. For example, certain embodiments may include an engagement element that is screwed onto shaft 12, snapped onto shaft 12, or the like. Similarly, it is contemplated to provide various shaped engagement elements 18 for cooperating with and engaging differently sized and shaped acetabular cups. Element 76 can be of any shape which maintains axis 59 in alignment with the polar axis of shell 72. Differently sized and shaped blades 34 may also be provided for cutting around differently sized and shaped acetabular cups. It is also contemplated to size these elements such that specific combinations of engagement elements and blades are provided for cutting out specific cups. Therefore, it is possible to provide a kit including differing engagement elements 18 and blades 34 that may be interchanged to properly cut around a specific acetabular cup.

Figure 9:
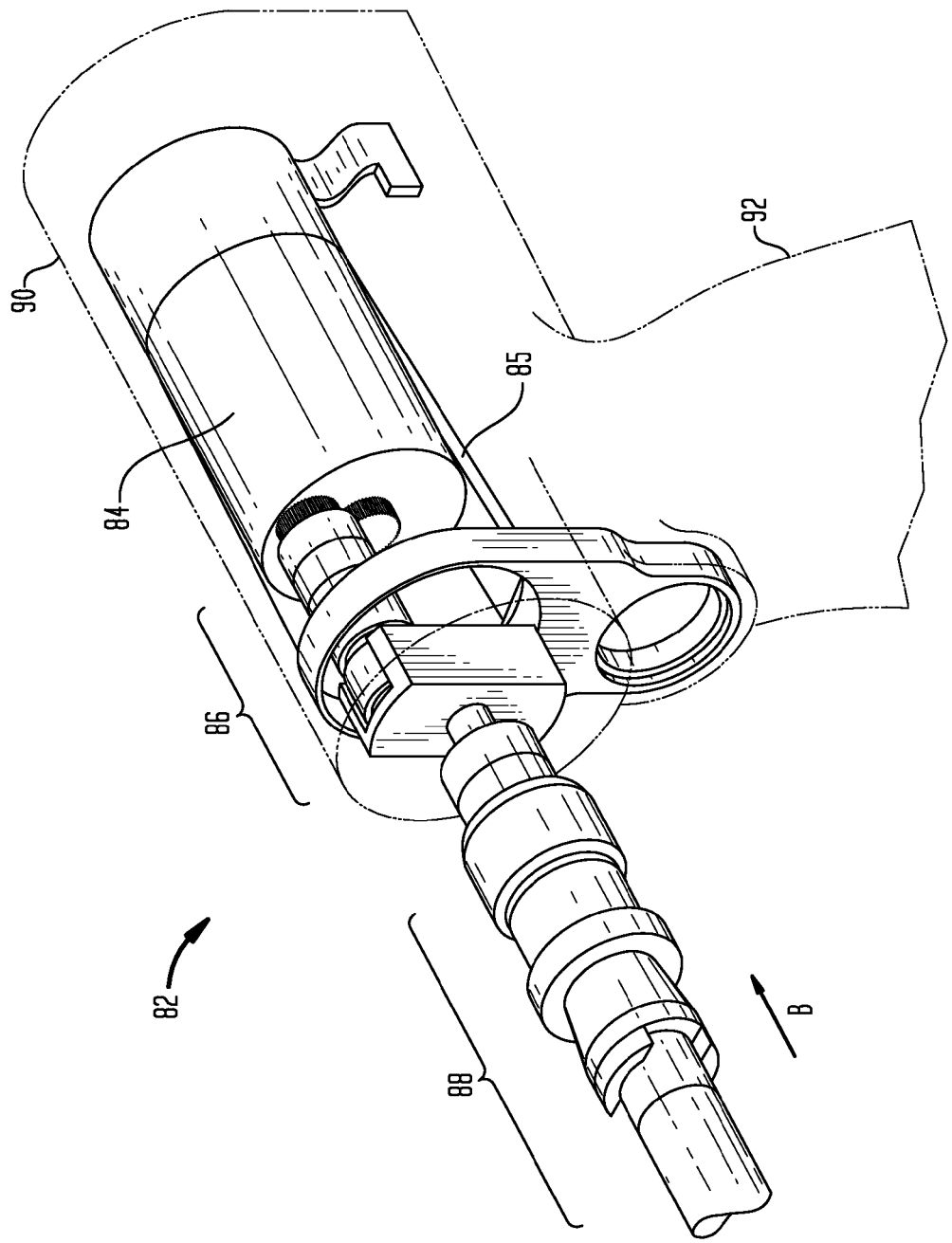
FIG. 9 is a cross sectional view of a handpiece for use with the removal instrument shown in FIG. 1.

In the preferred embodiment, as shown in FIGS. 1 and 2, second end 22 of elongate shaft 12 includes a male connector 80. This connector is suitable for linking instrument 10 with a powering device capable of providing oscillating or rotating motion to shaft 12 of instrument 10. There exist many different suitable powering devices, however, in accordance with a preferred embodiment, instrument 10 is linked with a variable control handpiece 82, as shown in FIG. 9 which produces an oscillating movement of +4° of rotation at a variable rate from approximately zero (0) to twelve thousand (12,000) times per minute. Handpiece 82 is a handheld device typically powered by a rechargeable battery or the like. As shown in the internal depiction of FIG. 9, handpiece 82 includes a motor assembly 84 which powers a drive train assembly 86 and female quick connector 88. It is noted that motor assembly 84 and drive train assembly 86 are preferably encased by a housing 90, as shown in FIG. 9. Handpiece 82 is also preferably provided with an actuation mechanism in the form of a trigger (not shown) for selectively providing oscillation to shaft 12 of instrument 10. In preferred embodiments, the trigger is situated with respect to a handle 92 so that a user may easily grip the handpiece and operate the trigger.

Figure 10:
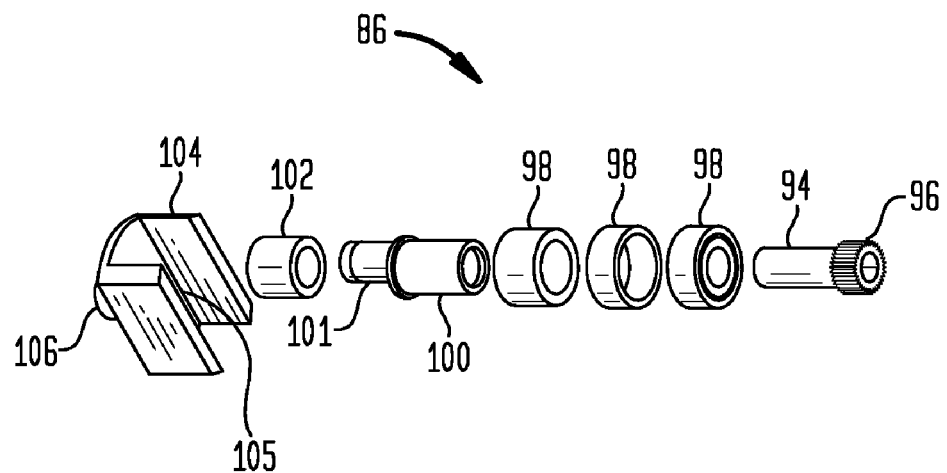
FIG. 10 is a perspective view of the drive train assembly shown in FIG. 9.
Figure 11:
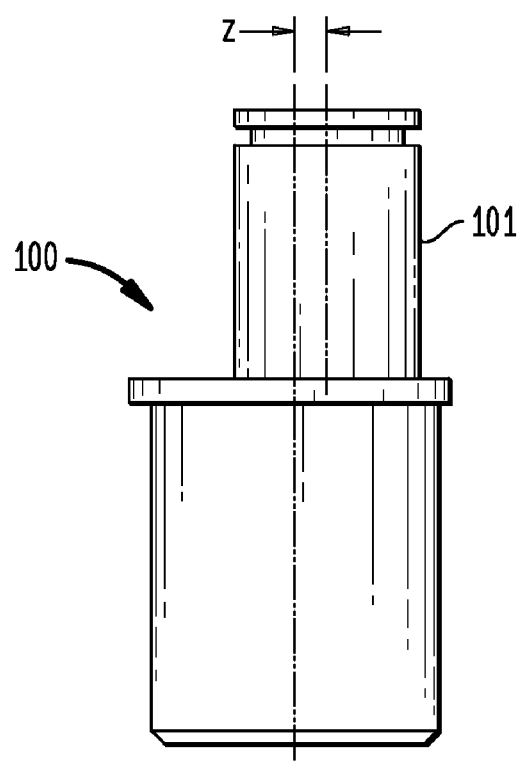
FIG. 11 is a side view of the offset second axle shown in FIG. 10.

As shown in the exploded view of FIG. 10, drive train assembly 86 includes a first axle 94 with one end having a gear 96 situated thereon. Gear 96 is configured to be driven by a complimentary gear 85 (shown in FIG. 9) that is directly connected to motor 84. Drive train assembly further includes a series of bearings 98, a second axle 100, roller 102 and yoke 104. Yoke 104 includes a channel or groove 105 for receiving roller 102 and an end portion 106. Second axle 100 is in rotatable communication with first axle 94, and, as best shown in FIG. 11, includes an offset portion 101. Offset portion 101 is offset a distance z from the main body of second axle 100 and is adapted to connect with roller 102. In the fully assembled handpiece 82, end portion 106 of yoke 104 is rotatably connected to connector 88.

In operation, motor 84 rotates first axle 94, which in turn rotates second axle 100. Bearings 98 are designed to provide smooth rotation of the various components. The rotation of second axle 100 provides an off center rotation to offset portion 101, which in turn causes yoke 104 to oscillate. The amount of oscillation is a direct result of the amount of offset distance z. In a preferred embodiment, the amount of oscillation is approximately four degrees in a clockwise direction and four degrees in a counter clockwise direction. However, in other embodiments, the oscillation may be any amount or complete rotation. The oscillating motion is ultimately translated to female quick connector 88, and to instrument 10 upon connection thereto. It is noted that female quick connector 88 may be well known in the art. Typically such a device would allow the reception of male connector 80 upon movement of female connector 88 in the direction depicted by arrow B, as shown in FIG. 9.

The operation of the removal instrument 10 in conjunction with handpiece 82, to remove a previously implanted acetabular cup 72 will now be discussed. Initially, a surgeon will be required to perform the necessary steps to expose the acetabular cup that is to be removed. Such a surgery includes, among various other steps, making an incision to uncover the interior anatomy, clearing away the hip joint and removing the femoral component from the acetabular cup. With acetabular cup 72 properly exposed, the surgeon may first determine the type of cup that has been implanted. This determination may allow the surgeon to select a proper engagement element 18 and blade 34. Tables or the like may be provided for aiding the surgeon in selecting the proper components from a list of components. Once these components are selected, the instrument 10 may be assembled accordingly. This may involve merely the steps of attaching engagement element 18 to first end 20 of shaft 12 and attaching blade 34 to pivoting element 36, or may also include the aforementioned complete assembly of the other components of instrument 10 (e.g.—the insertion of slide bar 54 into shaft 12). With instrument 10 properly assembled, it may be connected to handpiece 82. The simple connection of these devices was discussed above in the section relating to quick connection 88.

Figure 12:
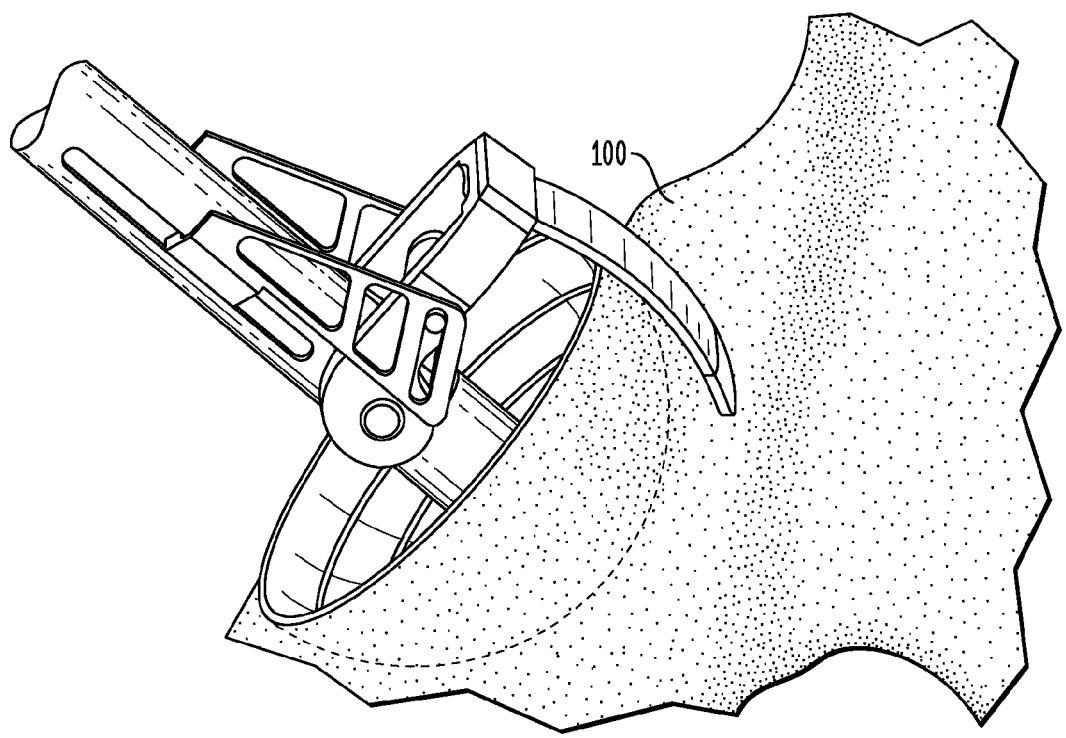
FIG. 12 is a perspective view of the removal instrument shown in FIG. 1 seated in an implanted acetabular cup, with a blade portion not engaged.

The surgeon then seats or locks engagement element 18 in acetabular cup 72. As described above, this seating may prevent the instrument 10 from pivoting or otherwise moving with respect to cup 72. At this point, instrument 10 is situated with blade 34 disposed in the fashion shown in FIG. 12. Essentially, blade 34 is not in engagement with any portion of bone 100. The surgeon may then activate handpiece 82 by depressing trigger 98. This causes most of instrument 10 to oscillate, including the entire elongate shaft 12 and especially blade 34. However, the cooperation between elongate shaft 12 and handle 16 allows for the handle to not oscillate. Therefore, the surgeon is free to grasp and operate handle 16 with his or her free hand. It is noted that the offset nature of blade 34 with respect to shaft 12 allows for the easy cutting of bone upon the oscillation of the entire instrument 10.

Figure 13:
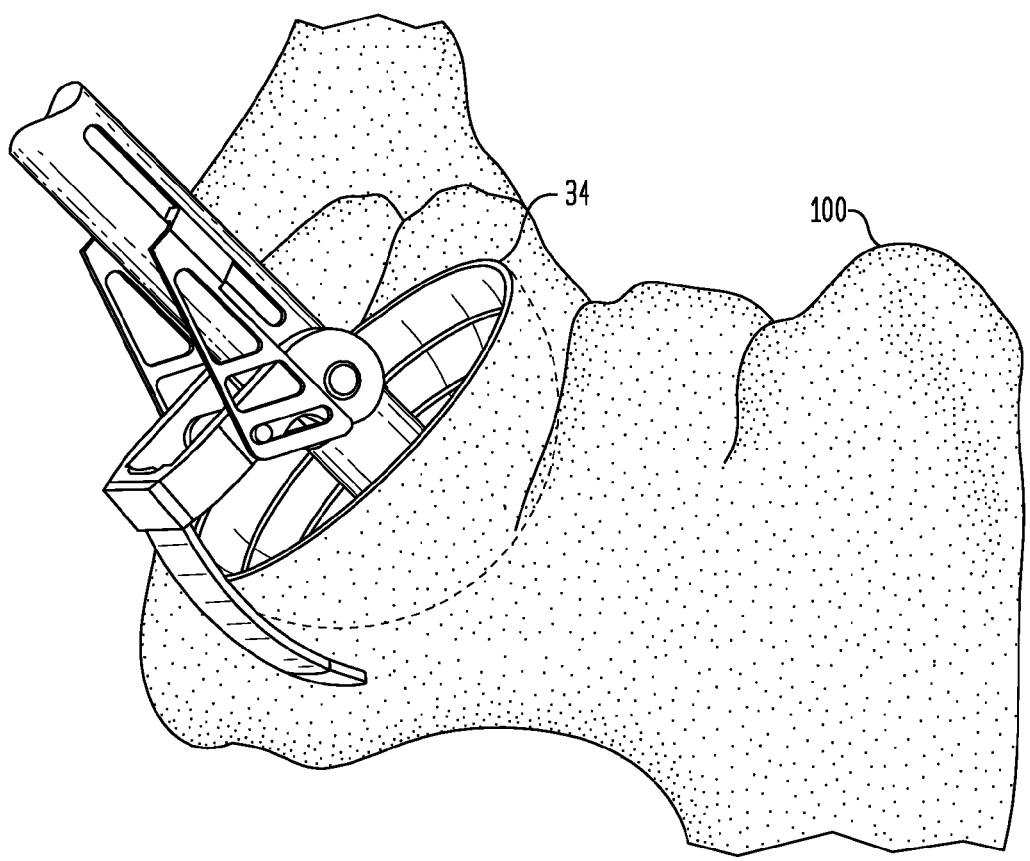
FIG. 13 is a perspective view of the removal instrument shown in FIG. 1 seated in an implanted acetabular cup, with a blade portion engaged.

Upon movement of handle 16 in the direction of arrow A (shown in FIG. 1), the surgeon causes blade 34 to engage bone 100, as shown in FIG. 13. Clearly, the oscillating movement provided to the blade by handpiece 82 necessarily causes the cutting of bone 100 upon contact with blade 34. However, this initial cut cuts only a small width of the bone around the total circumference of cup 72 preferably being slightly larger than the width of head 37. Therefore, it is noted that in preferred methods, the surgeon typically would slowly operate handle 16 to slowly sink blade 34 into bone 100, while also rotating instrument 10 around the circumference of cup 72. A surgeon should perform this combination translation and rotation method slowly, so as not to cause damage to blade 34. Performing these steps, especially the rotational movement of instrument 10, in excess speed may cause blade 34 to bend or sheer. Alternatively, in other embodiments, a surgeon may sink and remove blade 34 (by operating handle 16 in opposing directions) independently of the rotation of instrument 10. Sequential cuts would therefore begin to create a cut surface that extends completely around the entire circumference of acetabular cup 72. However, clearly this would require an increased time for completely cutting around cup 72. Further, certain embodiments may include a blade that includes a cutting surface that faces in the direction that instrument 10 is rotated. This design may aid in the cutting of bone while rotating. Finally, in other embodiments, the cutter blade may be rotated completely around axis 59 of shaft 12 if a non-oscillating handpiece or the like is used. In this case, only small advances of handle 16 should be used during cutting.

Figure 14:
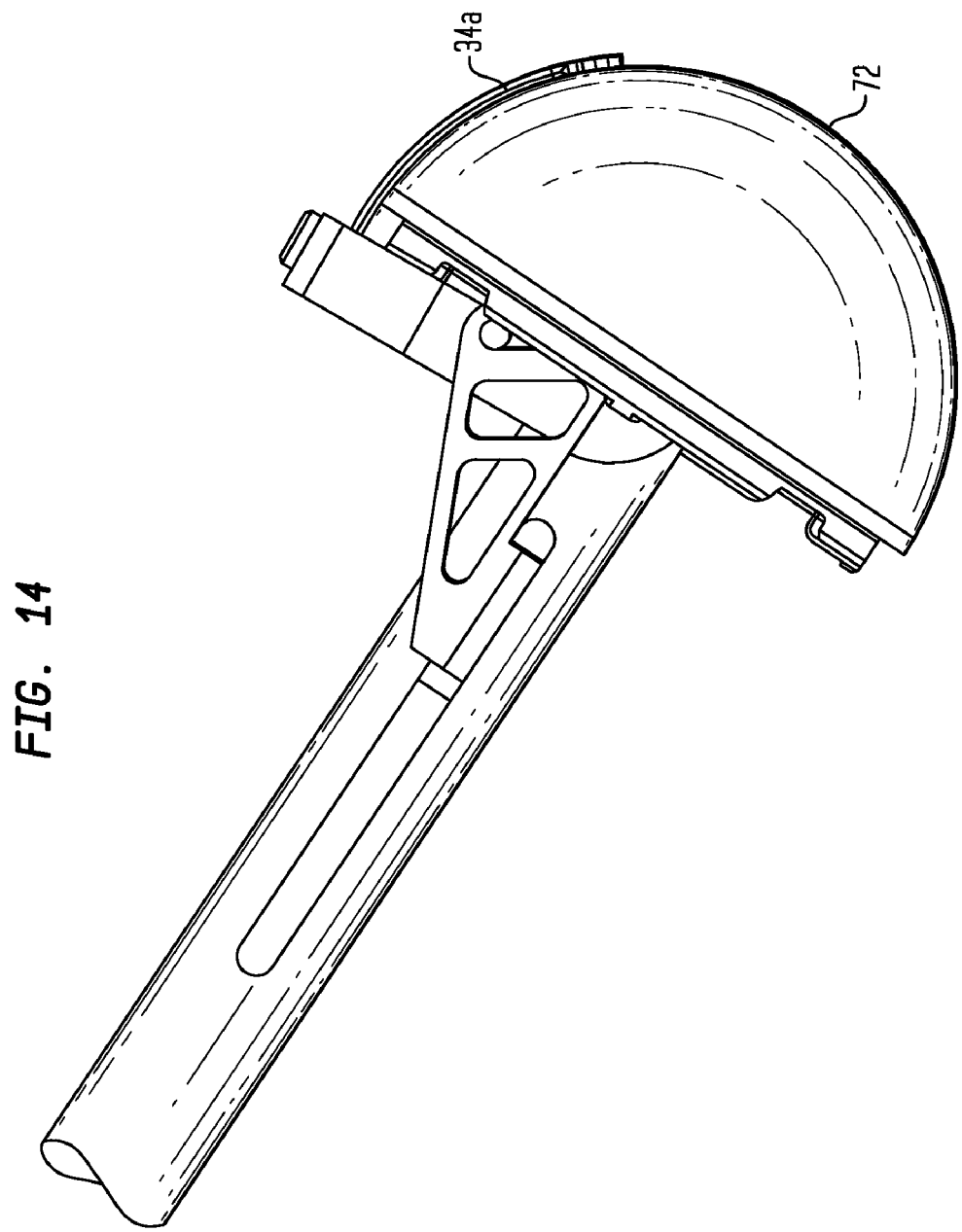
FIG. 14 is a perspective view of the removal instrument shown in FIG. 1 seated in an acetabular cup, with a short blade portion completely extended.
Figure 15:
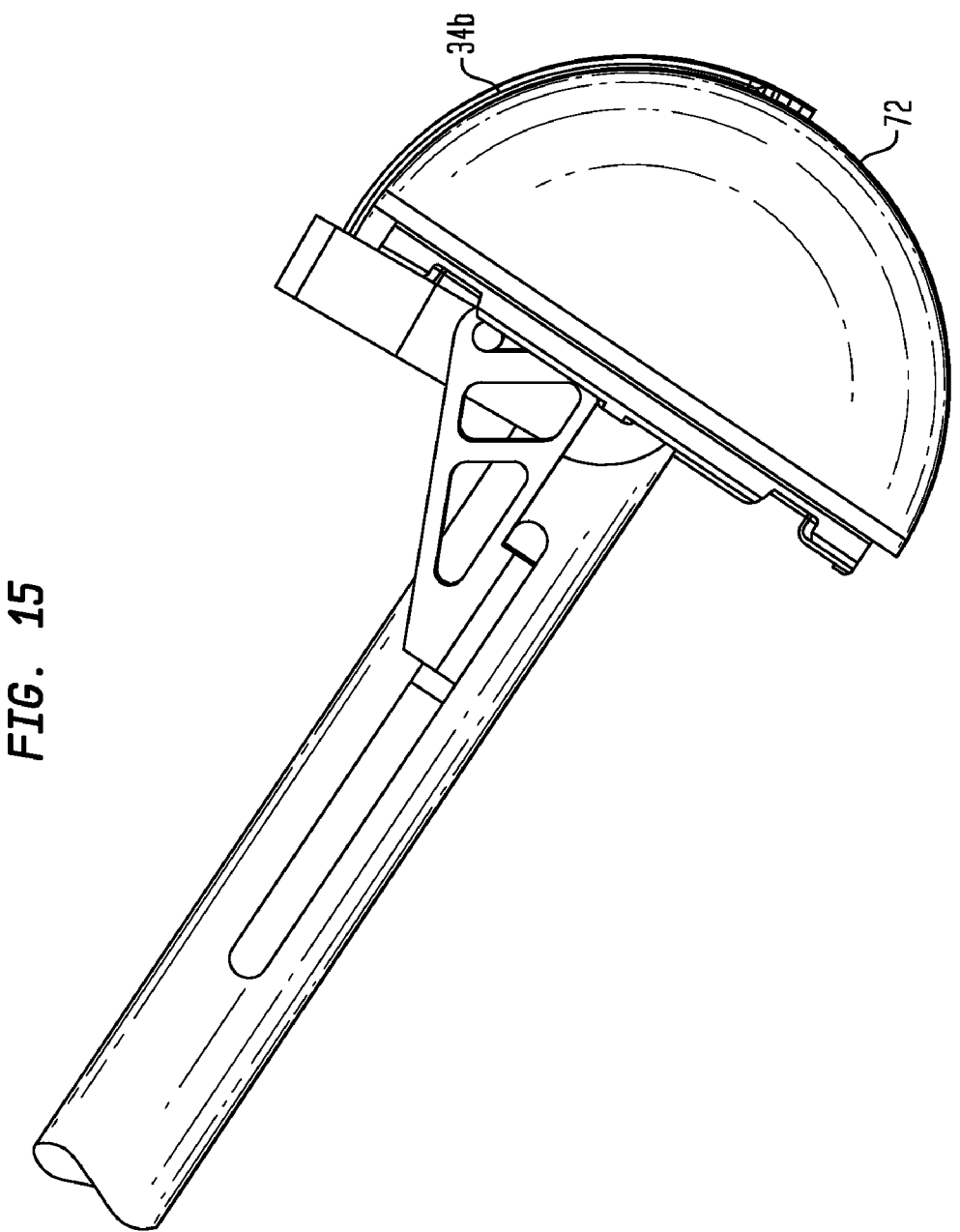
FIG. 15 is a perspective view of the removal instrument shown in FIG. 1 seated in an acetabular cup, with a long blade portion completely extended.
Figure 16:
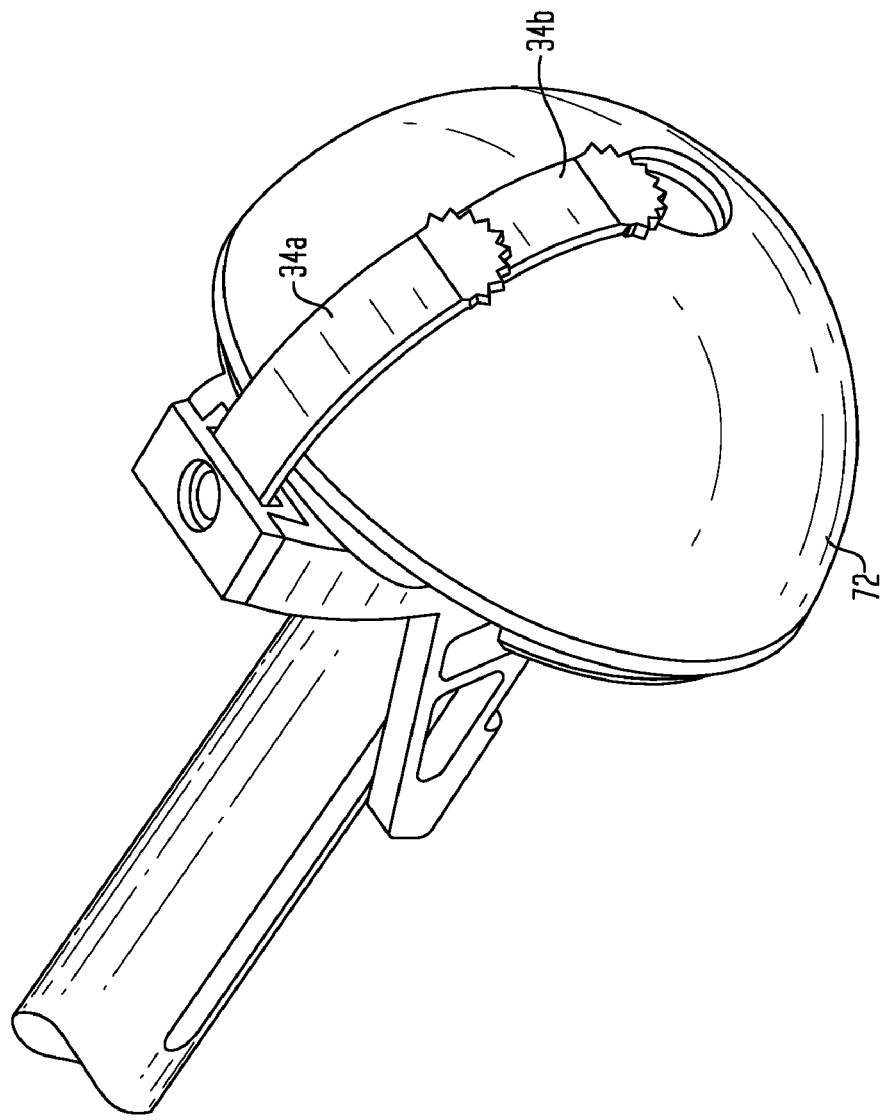
FIG. 16 is a bottom perspective view of the removal instrument shown in FIG. 1 seated in an acetabular cup, depicting both the short blade portion and long blade portion depicted in FIGS. 14 and 15, respectively.

It is also contemplated to perform these cuts utilizing two different blades, 34a and 34b. As shown in FIG. 14, complete operation of handle 16 (i.e.—complete sliding in direction A) causes an initial shorter blade 34a to extend only partially around cup 72. This would clearly only allow for the cutting of approximately seventy percent (70%) of bone residing around the outside surface of cup 72. Therefore, a relatively small portion of bone connected to the center or polar area of the exterior surface of cup 72 would remain. Therefore, as shown in FIG. 15, a longer blade 34b may be utilized once the cuts are completed with blade 34a. The aforementioned removably attached nature of the blades typically allows for the easy interchangeability between blades 34a and 34b. As clearly shown in FIG. 15, the length of blade 34b allows for the cutting of the relatively small portion of bone connected to the center or polar area of the exterior surface of cup 72, and thus the completion of cuts around cup 72. It is noted that in certain embodiments, it is necessary to first make initial cuts with shorter blade 34a because, absent such cuts, there is not enough clearance for a cut to be initiated by blade 34b. However, it may indeed be possible to provide other designs that would allow for a complete cut to be made utilizing a single blade. In accordance with a preferred embodiment, FIG. 16 shows a comparison depiction of blades 34a and 34b in their respective fully extended positions.

In other embodiments, as discussed above, a single blade may be utilized that leaves a small connection between the bone and the exterior surface of the cup. Depending upon the length and curvature of the blade this connection may be of various sizes, but is usually small. Nevertheless, with the significant cut surface already created, cup 72 may be capable of being easily removed. In fact, in many cases, cup 72 may be removed without the use of any additional instruments (i.e.— by hand). Therefore, the final step of the process in accordance with these embodiments, would be the actual removal of acetabular cup 72. Irregardless of method employed, with the cup removed, the surgeon now has a relatively smooth surface and properly shaped surface for the implanting of a new cup or to further prepare the acetabular surface such as with a typical acetabular reamer. Once the surface of the acetabulum is prepared, a new acetabular cup including bearing may be implanted.

Figure 17:
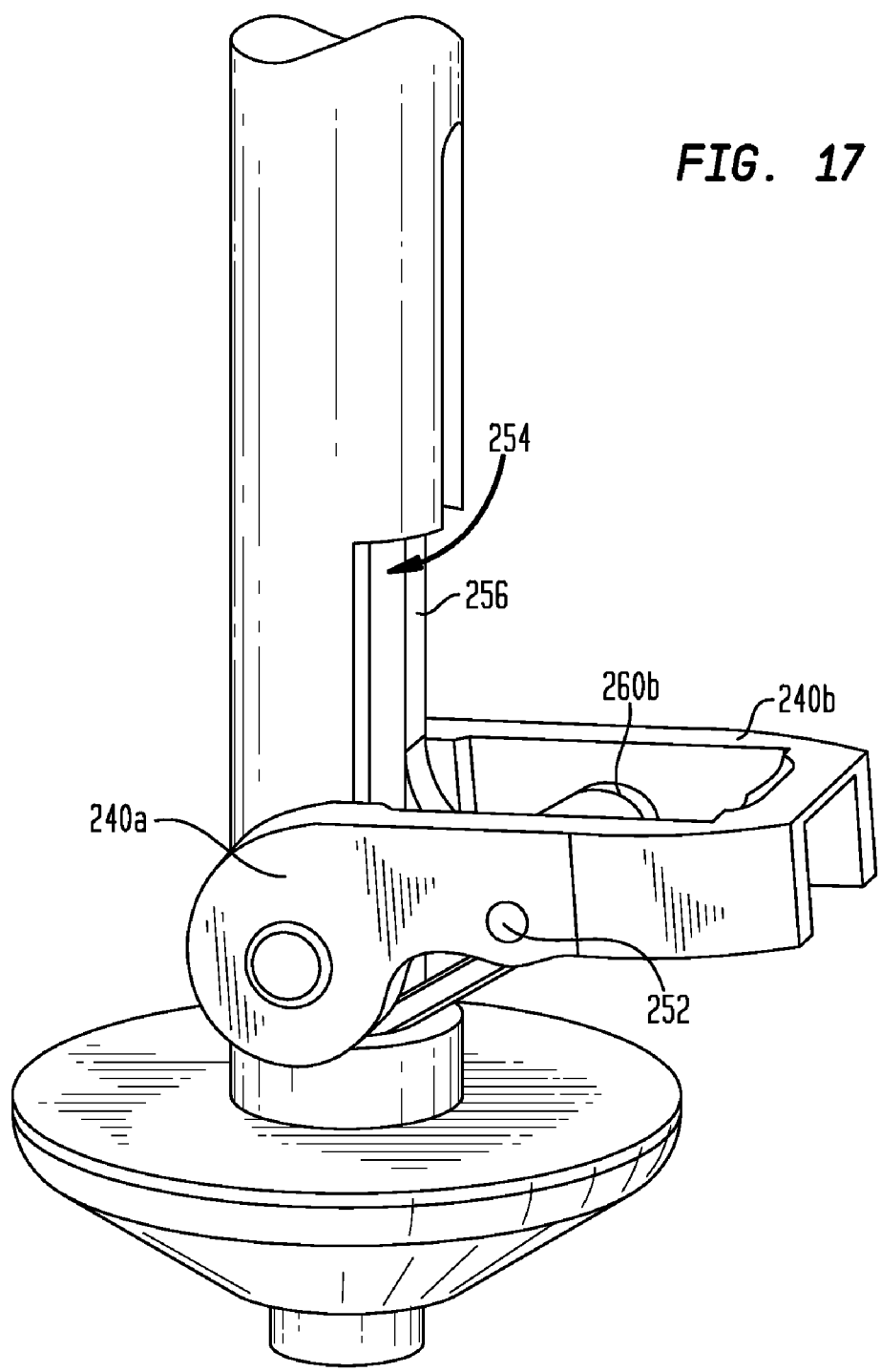
FIG. 17 is a perspective view of a removal instrument according to another embodiment of the present invention.
Figure 18:
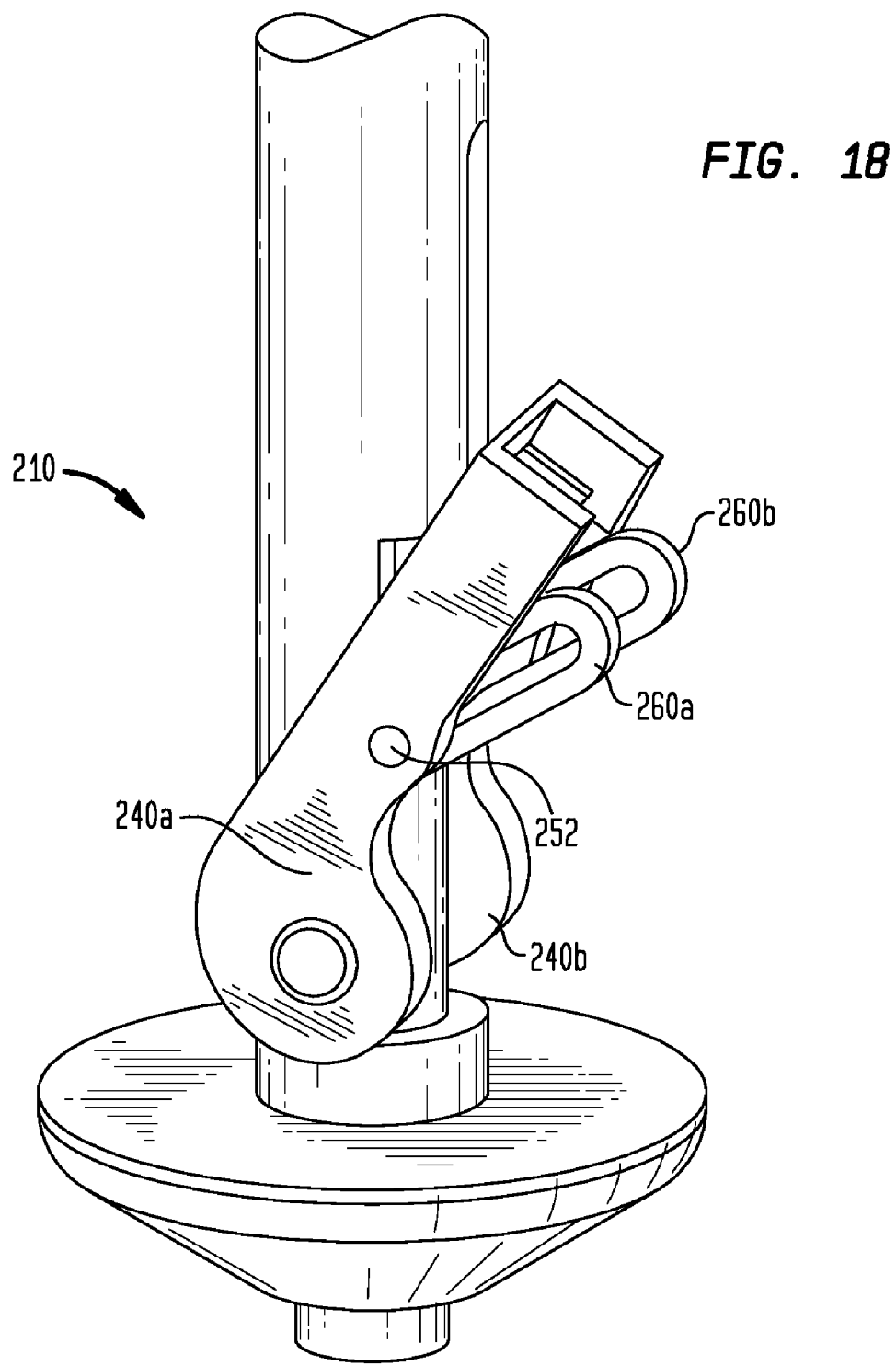
FIG. 18 is a side perspective view of the removal instrument shown in FIG. 17.
Figure 19:
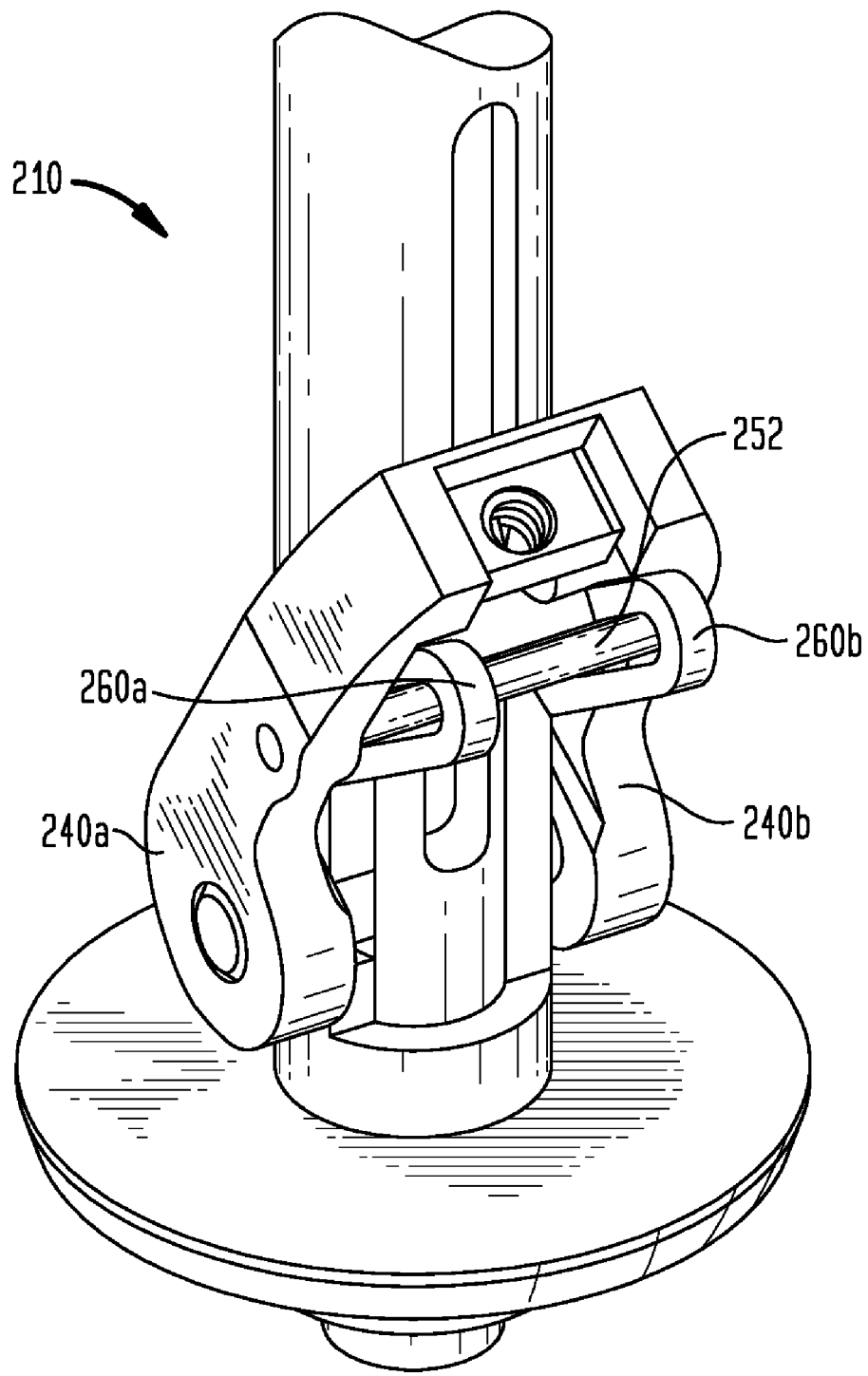
FIG. 19 is a front perspective view of the removal instrument shown in FIG. 17.

FIGS. 17, 18 and 19 depict an alternate embodiment instrument 210, in accordance with another embodiment of the present invention. Essentially, instruments 210 in accordance with this embodiment differ from the other embodiment shown in FIGS. 1-16 in the design of and cooperation between pivoting element 236 and slide bar 254. As shown in FIGS. 17-19, instrument 210 includes a slide bar 254 having two receiver plates 260a and 260b, each offset from an elongate body 256 of slide bar 254. These receiver plates are designed so that they may be situated between spaced legs 240a and 242a of pivoting element 236, and engage an extension pin 252 that extends between the legs. The operation of instrument 210 is similar in nature to the above described instrument 10. However, the design of instrument 210 provides a lower profile design that may allow instrument 210 to be utilized in smaller incisions or for damaging less soft tissue within the hip joint than the aforementioned instrument 10.

FIGS. 20 and 21, as mentioned above, depict a quick connection device 300 for easily attaching and a detaching blade 334 to a pivoting element 336. In this design, pivoting element 336 includes a slot or channel 338 having a smaller channel or slot 340. Channels 338 and 340 cooperate with a slidable arm 342 and pin 344, respectively. In the completed device 300, pin 344 is disposed in a hole 346 of arm 342, such that pin 344 extends into slot 340. A spring 348 is also included for biasing arm 342 in a direction depicted by arrow D. Arm 342 is capable of being moved in the direction of arrow D, as well as the opposite direction thereof. In operation, in order to attach blade 334, a surgeon or the like simply moves arm 342 in a direction opposite to that of arrow D. In this position, blade 334 may be engaged with pivoting element 336. Thereafter, arm 342 may be released so that spring 348 biases the arm and captures blade 334. This captured position is shown in FIG. 21. Absent an additional force applied to arm 342, spring 348 will keep blade 334 captured and engaged with pivoting element 336. It is noted that spring 348 should be strong enough to provide sufficient force to keep arm 342 biased in the direction of arrow D. It is contemplated that various other quick connect devices are envisioned that work in similar fashions for allowing the easy attaching and detaching of a blade to instrument 10.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of removing an acetabular cup from an acetabulum comprising:
providing a powered apparatus including an elongate shaft having a first end and a second end, a cutting element attached adjacent the first end, and a powered handpiece connected to the second end;
placing a portion of the first end of the elongate shaft within the acetabular cup;
operating the powered handpiece so as to make at least one cut in a bone surface adjacent an outer surface of the acetabular cup;
manipulating a handle engaged with the elongate shaft to determine the depth of the cut in the bone surface, wherein the step of manipulating the handle includes freely moving the handle in two longitudinal directions with respect to the shaft; and
removing the acetabular cup from the acetabulum.

2. The method according to claim 1, further comprising the step of rotating the powered apparatus while manipulating the handle to create a cut around the acetabular cup.

3. The method according to claim 1, further comprising the step of selecting an appropriately sized cutting element corresponding to the size of the acetabular cup.

4. The method according to claim 1, further including the step of selecting an engagement element for engaging the acetabular cup and attaching the engagement element to the first end of the elongate shaft, wherein the placing step includes placing the engagement element within the acetabular cup.

5. The method according to claim 1, wherein freely moving the handle in two longitudinal directions with respect to the shaft causes pivoting of the cutting element.

6. The method according to claim 1, wherein the operating step includes providing a rotating cutting motion to the cutting element.

7. The method according to claim 6, wherein the manipulation of the handle is independent to the rotating cutting motion.

8. The method according to claim 1, wherein the operating step includes providing a rotating cutting motion to the cutting element, the rotating cutting motion between four degrees in a clockwise direction and four degrees in a counterclockwise direction.

9. A method of removing an acetabular cup from an acetabulum comprising:
providing a powered apparatus including an elongate shaft having a first end and a second end, a cutting element pivotally attached adjacent the first end, a handle slideably engaged with and capable of at least partial rotation around the elongated shaft, and a powered handpiece connected to the second end;

placing a portion of the first end of the elongate shaft within the acetabular cup;

operating the powered handpiece to provide a rotating cutting motion to the cutting element so as to make at least one cut in a bone adjacent the acetabular cup;

sliding the handle along the elongate shaft to pivot the cutting element to determine the depth of the cut in the bone surface adjacent the acetabular cup, the sliding of the handle being independent of the partial rotation of the handle around the shaft, wherein the sliding step includes freely sliding the handle in two longitudinal directions with respect to the shaft; and removing the acetabular cup from the acetabulum.

10. The method according to claim 9, further comprising the steps of selecting an appropriately sized cutting element and attaching the appropriately sized cutting element to the powered apparatus.

11. The method according to claim 9, wherein the rotating cutting motion is between four degrees in a clockwise direction and four degrees in a counter-clockwise direction.

12. The method according to claim 9, further comprising the steps of selecting an appropriately sized engagement element, attaching the engagement element to the first end of the shaft and engaging the engagement element within the acetabular cup.

13. The method according to claim 9, wherein the cutting element is curved.

14. The method according to claim 9, further comprising the step of attaching the powered handpiece to the second end.

15. A method of removing an acetabular cup from an acetabulum comprising:

providing an apparatus including an elongate shaft having a first end and a second end, and a handle slideably engaged with and capable of at least partial rotation around the elongated shaft;

pivotally attaching a cutting element adjacent the first end;

attaching a powered handpiece to the second end;

attaching an engagement element to the first end;

placing a portion of the engagement element within the acetabular cup;

operating the powered handpiece to provide a rotating cutting motion to the cutting element so as to make at least one cut in a bone adjacent the acetabular cup;

freely sliding the handle in two longitudinal directions along the elongate shaft to pivot the cutting element to determine the depth of the cut in the bone surface adjacent the acetabular cup, the sliding of the handle being independent of the partial rotation of the handle around the shaft; and removing the acetabular cup from the acetabulum.

16. The method according to claim 15, further comprising the step of selecting an appropriately sized cutting element.

17. The method according to claim 15, further comprising the step of selecting an appropriately sized engagement element.

* * * * *